United States Patent [19]

Jouin et al.

[11] Patent Number: 4,978,759

[45] Date of Patent: Dec. 18, 1990

[54] PROCESS FOR THE STEREOSPECIFIC SYNTHESIS OF OPTICALLY PURE 4-AMINO-3-HYDROXYCARBOXYLIC ACID DERIVATIVES

[75] Inventors: Patrick Jouin, Amiane; Dino Nisato, Saint Georges D'Orques; Bertrand Castro, Saint Aunes, all of France

[73] Assignee: Sanofi, S.A. and Institut National de la Sante et de la Recherche Medicale, Paris, France

[21] Appl. No.: 881,191

[22] Filed: Jul. 2, 1986

[30] Foreign Application Priority Data

Jul. 3, 1985 [FR] France ................................. 85 10181

[51] Int. Cl.⁵ .................. C07D 209/20; C07D 233/18; C07C 59/40; C07C 51/00

[52] U.S. Cl. ..................................... 548/497; 548/344; 548/543; 548/538; 548/498; 560/29; 560/39; 560/115; 560/148; 560/153; 560/158; 560/159; 560/169; 560/170; 560/179; 560/125; 562/444; 562/507; 562/567; 562/556; 562/561; 260/404; 260/410.9; 549/274; 549/333; 549/372

[58] Field of Search ............... 548/543, 497, 498, 344, 548/501; 260/404; 549/274; 560/29, 39, 169, 115, 125, 148, 153, 158, 159; 562/444, 507, 567, 556, 561

[56] References Cited

U.S. PATENT DOCUMENTS 3,503,993  3/1970  Blame ............................... 549/274
4,264,771  4/1981  Steglich et al. ..................... 562/567
4,547,516  10/1985 Bellini et al. ........................ 549/274

OTHER PUBLICATIONS

Porter et al., "Synthesis, resolution and characterization of ring substituted phenylalanines and tryptophans", Int. J. Peptide Protein Res. 30, 1987, pp. 13–21.
Albertson, "The Synthesis of Amino Acids from Ethyl Acetamidomalonate and Ethyl Acetamidocyanoacetate. III. The Use of Primary Halides", J.Am. Chem. Soc., vol. 68, 1946, pp. 450–453.
Snyder et al., "Synthetic Amino Acids Syntheses from Acetamidomalonic Ester", J. Am. Chem. Soc., vol. 67, 1945, pp. 310–312.
The Merk Index, 9th Ed., 1976, Organic Name Reactions, ONR-85–86.
Tarbell et al., "New Method To Prepare N-t-Butoxycarbonyl Derivatives and the Corresponding Sulfur Analogs from Di-t-Butyl Dicarbonate or di-t-Butyl Dithiol Dicarbonates and Amino Acids", Proc. Nat. Acad. Sci., U.S.A., vol. 69, No. 3, 3/72, pp. 730–732.
Roberts et al., Chimie Organique Moderne, Paris, 1967, pp. 521–522.
Katsuki et al., Bull. of Chem. Soc. of Japan, vol. 49(11), pp. 3287–3290 (1976).

Primary Examiner—David B. Springer
Attorney, Agent, or Firm—Davis Hoxie Faithfull & Hapgood

[57] ABSTRACT

The process described makes it possible to obtain optically pure 4-amino-3-hydroxycarboxylic acids by means of a series of stereoselective steps. The starting material is an alpha-amino acid in the L or D configuration, with which Meldrum's acid is reacted. The resulting pyrrolone derivative is reduced prior to opening of the pyrrolidine ring. The invention also relates to the new products obtained by the said process and to the pyrrolone derivatives obtained as intermediates.

13 Claims, No Drawings

PROCESS FOR THE STEREOSPECIFIC SYNTHESIS OF OPTICALLY PURE 4-AMINO-3-HYDROXYCARBOXYLIC ACID DERIVATIVES

The present invention relates to a process for the synthesis of optically pure 4-amino-3-hydroxycarboxylic acid derivatives, each step of this process being carried out stereoselectively.

According to another feature, the present invention relates to the new optically pure 4-amino-3-hydroxycarboxylic acid derivatives obtained by this process.

The process according to the invention makes it possible to prepare statine and its derivatives. These compounds are useful in particular for the preparation of peptides which inhibit renin.

The present invention also relates to the new optically active pyrrolidinedione and pyrrolidinone derivatives obtained as synthesis intermediates in the process according to the invention.

The following abbreviations will be used in the description of the present invention and in the claims:

| | |
|---|---|
| Leu | L-leucine |
| Phe | L-phenylalanine |
| Sta | statine = (3S,4S)-4-amino-3-hydroxy-6-methylheptanoic acid |
| AcOH | acetic acid |
| AcOEt | ethyl acetate |
| Boc | tert.-butyoxycarbonyl |
| Z | benzyloxycarbonyl |
| TLC | thin layer chromatography |
| DMSO | dimethyl sulfoxide |
| MeOH | methanol |
| Meldrum's acid | 2,2-dimethyl-1,3-dioxane-4,6-dione. |

The asymmetric carbons are shown as C.

Several methods for the synthesis of 4-amino-3-hydroxycarboxylic acid derivatives have been described, especially the preparation of (3S,4S)-4-amino-3-hydroxy-6-methylheptanoic acid: statine.

None of these methods is entirely stereospecific and a step is always required to separate the diastereoisomers. The new methods of synthesis which have been described to data have endeavored in particular to improve the results obtained in this step (Bull. Soc. Chim. Fr., 1983, 230-232). Despite its title: "The Stereoselective Synthesis of threo-3-hydroxy-4-amino Acids", the article published in Bull. Chem. Soc. Jap., 1976, 49 (11), 3287-3290, does not solve the problem of the stereospecificity of the synthesis. The authors describe the preparation of certain 4-amino-3-hydroxycarboxylic acids, for example statine, from the corresponding amino acid in accordance with the following simplified reaction scheme:

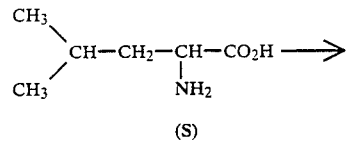

(S)

-continued

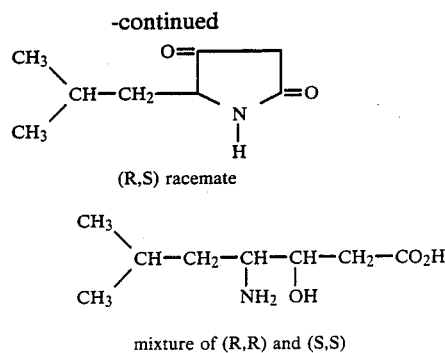

(R,S) racemate

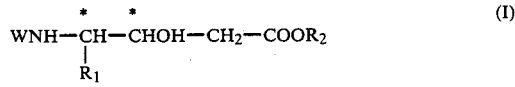

mixture of (R,R) and (S,S)

The intermediate pyrrolidinedione is a racemate; it then undergoes stereoselective reduction, leading to the mixture of diastereoisomers (R,R and S,S) in the cis configuration.

The present invention relates to a process for the stereospecific preparation of optically pure (3R,4R)-4-amino-3-hydroxycarboxylic or (3S,4S)-4-amino-3-hydroxycarboxylic acid derivatives of the formula:

$$WNH-\overset{*}{C}H-\overset{*}{C}HOH-CH_2-COOR_2 \qquad (I)$$
$$\underset{R_1}{|}$$

in which:
W is hydrogen or an N-protecting group;
R₁ represents a linear or branched alkyl radical having from 1 to 6 carbon atoms, such as methyl, ethyl, n-propyl, isopropyl, n-butyl, isobutyl, tert.-butyl, 1-methylpropyl, n-pentyl or n-hexyl, a methoxy-lower alkyl radical such as methoxyethyl, a benzyloxy-lower alkyl radical, a methylthio-lower alkyl radical such as methylthiomethyl, methylthioethyl, a phenylthio-lower alkyl radical, a benzylthio-lower alkyl radical, an amino-lower alkyl radical which is free or substituted by a protecting group on the amine group, such as 4-aminobutyl or 4-benzyloxycarbonylaminobutyl, a (lower alkyl-)amino-lower alkyl radical such as methylamino-, ethylamino-, isopropylamino- or tert.-butylamino-ethyl, a (lower dialkyl)amino-lower alkyl radical such as dimethylamino-, diethylamino-, di-n-propylamino- or di-n-butylamino-ethyl, a hydroxy-lower alkyl radical such as hydroxymethyl or 1-hydroxyethyl, a free or esterified carboxy-lower alkyl radical such as carboxymethyl or carboxyethyl, a free or alkylated carboxamido-lower alkyl radical, a lower alkyl radical substituted at the same time and on the same carbon atom by an amine and a free or esterified carboxyl, a linear or branched alkenyl radical having from 2 to 6 carbon atoms, a methoxy-lower alkenyl radical such as methoxyvinyl, a phenoxy-lower alkenyl radical, a benzyloxyalkenyl radical, a methylthio-lower alkenyl radical such as methylthiovinyl, a phenylthio-lower alkenyl radical, a benzylthio-lower alkenyl radical, an amino-lower alkenyl radical which is free or protected on the amine group, such as aminoallyl, a (lower alkyl)amino-lower alkenyl radical such as methylamino-, ethylamino-, isopropylamino- or tert.-butylamino-allyl, a (lower dialkyl)amino-lower alkenyl radical such as dimethylamino-, diethylamino-, di-n-propylamino- or di-n-butylamino-allyl, a free or esterified carboxy-lower alkenyl radical, a free or alkylated carboxamido-lower alkenyl radical or a linear or branched alkynyl radical having from 2 to 6 carbon atoms, or $R_1$ represents one of the radical of the general formulae:

in which:

Cy represents an aromatic or alicyclic hydrocarbon radical or a heterocyclic radical containing an oxygen or sulfur atom or one or two nitrogen atoms, Cy optionally being mono-, di- or tri-substituted by hydroxyl, lower alkyl, lower alkoxy, trifluoromethyl, nitro or halogeno radicals, A represents a single bond, a linear or branched alkylene radical having from 1 to 5 carbon atoms or a linear or branched alkenylene radical having from 2 to 5 carbon atoms, A' represents a linear or branched alkylene radical having from 1 to 5 carbon atoms or a linear or branched alkenylene radical having from 2 to 5 carbon atoms, and $R_3$ represents an S-protecting group; $R_1$ being preferably a linear or branched alkyl radical having 1 to 6 carbon atoms, a benzyl, a cyclohexylmethyl, a methylthio-lower alkyl, a benzyloxy-lower alkyl, an amino-lower alkyl which is free or substituted on the alkyl group by an N-protecting group, or an indol-3-ylmethyl, and $R_2$ represents hydrogen, an alkali metal or alkaline earth metal, a lower alkyl or a benzyl which is unsubstituted or substituted by a lower alkyl group, a halogen or a nitro group.

In the present context, the terms referred to above have the following meanings:

"lower alkyl" denotes saturated aliphatic hydrocarbon radicals containing up to 4 carbon atoms, such as methyl, ethyl, n-propyl, isopropyl, n-butyl, isobutyl or tert.-butyl;

"lower alkoxy" denotes the hydroxyl group substituted by a lower alkyl radical such as defined above;

"aromatic or alicyclic hydrocarbon radical" denotes a phenyl or naphthyl radical or a cycloalkyl radical having 3 to 7 carbon atoms, such as cyclopropyl, cyclobutyl, cyclopenyl, cyclohexyl or cycloheptyl;

"heterocyclic radical" denotes a furyl, benzofuryl, thienyl, benzothienyl, pyrrolyl, pyridyl, piperidyl, morpholyl, piperazinyl, N-(lower alkyl)piperazinyl, indolyl or 1H-imidazolyl radical;

"S-protecting group" denotes an easily removable protecting group for mercapto groups, for example an aralkyl group such as benzyl, or a substituted aralkyl group such as a p-nitrobenzyl;

"N-protecting group" is understood as meaning a protecting group which is normally used in peptide chemistry, for example an alkylcarbonyl group such as formyl, acetyl or propionyl, an alkoxycarbonyl group such as tert.-butoxycarbonyl, an alkoxyalkylcarbonyl group such as methoxyacetyl or methoxypropionyl, an alkoxycarbonyl group such as methoxyacetyl or methoxycarbonyl, an aralkoxycarbonyl group such as benzyloxycarbonyl, a substituted aralkoxycarbonyl group such as p-nitrobenzyloxycarbonyl, a trityl or methoxytrityl group or an arylsulfonyl group such as p-toluenesulfonyl. The preferred N-protecting groups are the tert.-butoxycarbonyl group (Boc) or the benzyloxycarbonyl group (Z).

The process for the stereospecific preparation of the 4-amino-3-hydroxycarboxylic acid derivatives of the formula (I) comprises reacting Meldrum's acid with a protected, optically pure amino acid, in the D or L configuration, of the formula:

in which W' represents an N-protecting group such as Boc or Z, and $R_1$ has the meaning indicated above, in a basic medium, in the presence of an activator for the amino acid (II) or of a coupling agent, to give the compound (III); heating in a solvent at between 30° C. and 100° C. gives the compound (IV-IVa) in 2 tautomeric forms in equilibrium, in which the chirality of the carbon atom carrying the substituent $R_1$ is preserved.

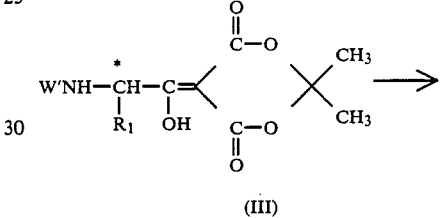

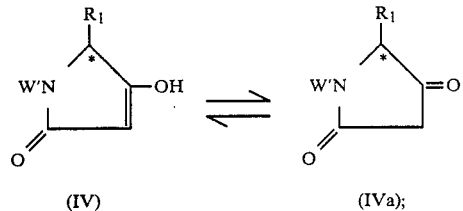

(IV-IVa) is reduced with a metal borohydride in an acid medium to give (V) in the cis configuration.

The ring is then opened to give (I) in which W=W', either in an acid medium in the case where W' represents an N-protecting group which is stable in an acid medium, such as Z, or in a basic medium in the case where W' represents a sterically hindered N-protecting group which is labile in an acid medium, such as Boc; the compound (I) in which W=H is obtained by deprotecting the nitrogen by the known methods.

In accordance with another feature, the present invention relates to the new products, namely (3R,4R)-4-amino-3-hydroxycarboxylic or (3S,4S)-4-amino-3-hydroxycarboxylic acid derivatives, obtained by the process according to the invention, which correspond to the formula:

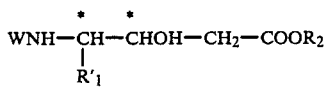 (VII)

in which W and $R_2$ have the same meanings as above and $R'_1$ has the same meaning as $R_1$ with the following restrictions: $R'_1$ cannot be methyl, isopropyl, isobutyl, benzyl which is unsubstituted or substituted by a nitro, omega-aminobutyl which is unsubstituted or substituted on the amine by a protecting group, or omega-amino-omega-carboxybutyl, The compounds (VII) are statine derivatives; like statine, they can be used in the synthesis of new peptide derivatives which inhibit renin.

The present invention also relates to the new optically pure 5-substituted 4-hydroxy-1,2-dihydro-2-pyrrolones, obtained as synthesis intermediates in the process according to the invention, which correspond to the formula:

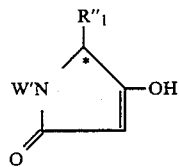 (IV)

They also exist in the tautomeric form of 2-substituted pyrrolidine-3,5-diones:

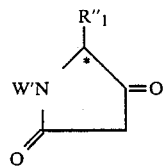 (IVa)

in which W' has the same meaning as above and $R''_1$ has the same meaning as $R_1$ with the restriction that $R''_1$ is other than 4-aminobutyl.

Finally, the present invention relates to the new optically pure pyrrolidinones in the cis configuration, obtained as synthesis intermediates in the process according to the invention, of the formula:

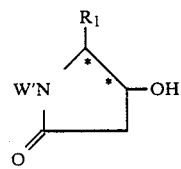 (V)

in which W' and $R''_1$ have the meanings indicated above.

The compounds which can be used as intermediates in the process of the present invention and which are illustrated by the formulae IV, IVa and V above can be jointly represented by the following formula:

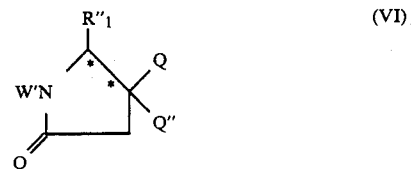 (VI)

in which W' and $R''_1$ are as defined above, Q represents a hydroxyl group, Q' is non-existent or represents a hydrogen atom, or alternatively Q and Q', taken together, represent an oxygen atom, and the broken line represents an additional bond in the case where Q' is non-existent, it being understood that, if Q' represents a hydrogen atom, the compound VI is in the (S,S) or (R,R) configuration.

The process according to the invention affords a totally new advantage, due especially to the stereospecificity of all its steps, which makes it possible to obtain each of the intermediates in an optically pure form and thus to avoid the separation of optical isomers. The chirality of the carbon atom in the alpha position of the starting amino acid is preserved throughout the process. Thus, after the condensation reaction with Meldrum's acid, heating gives the protected, optically pure pyrrolidinone (IV-IVa), which is subsequently reduced and then opened stereospecifically under the operating conditions according to the invention.

The starting material is a protected, optically pure alpha-amino acid of the formula:

 (II)

in which: W' represents a protecting group such as Boc or Z, and $R_1$ has the meaning indicated above.

Meldrum's acid is reacted with the amino acid (II) activated by an activator such as an acid chloride or an unsaturated chloroformate, or with the amino acid (II) in the presence of a coupling agent such as dicyclohexylcarbodiimide. The reaction is carried out in a medium rendered basic by the addition of a base such as pyridine or 4-dimethylaminopyridine, at a temperature between room temperature and −10° C., in an aprotic solvent such as methylene chloride or ethyl acetate, for several hours (from 1 to 5 hours).

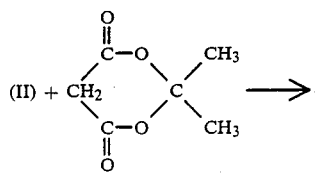

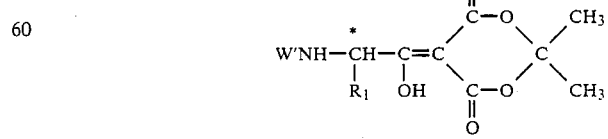

(III)

The reaction medium is treated, using the methods normally employed in organic chemistry, by adding a weakly acidic, aqueous solution and a saline solution and then drying the organic phase and evaporating it under reduced pressure. The resulting compound (III) is taken up in a solvent and heated at a temperature of between 30° C. and 100° C. The reaction medium is treated, using the methods normally employed in organic chemistry, to extract and purify the compound (IV–IVa) of the formula:

$$\text{(IV)} \rightleftharpoons \text{(IVa)}$$

with (IV): W'N–C(=O)– attached to a ring bearing R₁ and –OH (enol form); (IVa): the corresponding keto form with =O.

The reaction (III)→(IV–IVa) takes place stereoselectively. This is checked by measuring the optical rotation of (IV–IVa). (IV–IVa) is then reduced with a metal borohydride in an acid medium such as, for example, sodium borohydride, in the presence of acetic acid, in an aprotic solvent such as methylene chloride. If the substituent R₁ in the compound (IV–IVa) is not sensitive to hydrogenation, it is also possible to carry out a catalytic reduction under hydrogen pressure, for example in the presence of platinum oxide or Raney nickel. The reduced product is purified by a conventional technique, such as column chromatography, to give the compound (V):

(V): pyrrolidinone ring with R₁, –OH, W'N, and C=O substituents.

The reduction is stereospecific and leads to the compound in the cis configuration by asymmetric induction. Finally, the pyrrolidinone (V) is opened.

If the protecting group is stable in an acid medium, as is Z, for example, the opening of (V) is carried out in an acid medium, either in an organic solvent, such as dioxane, to give (I) in the acid form ($R_2$=H), or in an alcoholic solution $R_2$OH to give (I) in the form of an ester ($R_2$ being as defined above and other than hydrogen).

If the protecting group W' is sterically hindered and is labile in an acid medium, as is Boc, for example, the opening is carried out in a basic medium, i.e. either in the presence of sodium hydroxide to give (I) in the acid form ($R_2$=H), or in an alcoholic solution $R_2$OH, in the presence of the corresponding alcoholate, to give (I) in the ester form ($R_2$ being as defined above and other than hydrogen).

(V) $\xrightarrow{H^+ \text{ or } OH^-}$ $$\text{W'NH}-\overset{R_1}{\underset{*}{\text{CH}}}-\overset{*}{\underset{\text{OH}}{\text{CH}}}-\text{CH}_2-\text{CO}_2\text{R}_2$$

(I')

The chirality of the carbon atom carrying the secondary alcohol is preserved (Bull. Chem. Soc. Jap., 1976, 49 (II), 3287–3290). The nitrogen can then be deprotected by the methods known to those skilled in the art.

It is obvious that, if the starting material is an amino acid (II) in the L configuration, the compound (I) in the (3S,4S) configuration is obtained selectively, whereas if the starting material is the amino acid (II) in the D configuration, the compound (I) in the (3R,4R) configuration is obtained selectively.

The non-limiting examples which follow are given in order to illustrate the present invention.

The melting points (m.p.) are measured by the capillary tube method.

The specific rotations ($[\alpha]_D$) are measured at 25° C., the product being of molar concentration in methanol, unless indicated otherwise.

The proton nuclear magnetic resonance (NMR) spectra are run at 360 MHz in DMSO solution, the internal standard being hexamethyldisiloxane. In cases where the carbon 13 NMR spectrum is run, this is also done at 360 MHz in DMSO solution, the internal standard being hexamethyldisiloxane.

The following abbreviations are used:

| | |
|---|---|
| s | singlet |
| d | doublet |
| dd | doublet of doublets |
| m | multiplet |
| t | triplet |
| q | quadruplet |
| qd | doublet of quadruplets |

The chemical shifts (delta) are measured in ppm.

EXAMPLE 1

(3S,4S)-4-Tert.-butoxycarbonylamino-3-hydroxy-6-methylheptanoic acid (1) Dehydrated Boc-leucine:

5 g of Boc-Leu-OH.H₂O and 100 ml of toluene are mixed in a 500 ml round-bottomed flask with a ground glass neck, and azeotropic evaporation of the water is then carried out twice in succession in a rotary evaporator. The dehydrated product, in the form of an oil, is left overnight in a desiccator over phosphorus pentoxide.

(2)
5-(2-Tert.-butoxycarbonylamino-1-hydroxy-5-methyl-pentylidene)-2,2-dimethyl-1,3-dioxane -4,6-dione Compound (III): W'=Boc, $R_1$=CH₂CH(CH₃)₂.

The dehydrated Boc-leucine obtained previously is taken up in 100 ml of methylene chloride to which 3 g of Meldrum's acid are added, the medium is then stirred at −5° C., 5.6 g of 4-dimethylaminopyridine are added and 2.6 ml of isopropenyl chloroformate diluted in 10 ml of methylene chloride are then added dropwise over 30 minutes. After 2 hours, the reaction medium is washed with 200 ml of a 5% solution of potassium bisulfate and then with water, dried over sodium sulfate and evaporated under reduced pressure at a temperature below 40° C. The reaction is followed by TLC, eluting with the mixture AcOEt/MeOH/AcOH:95/3/2; Rf=0.60.

(3)
(S)-1-Tert.-butoxycarbonyl-4-hydroxy-5-isobutyl-1,2-dihydro-2-pyrrolone

Compound (IV-IVa): W'=Boc, $R_1$=CH$_2$CH(CH$_3$)$_2$

The crude product obtained previously is taken up in 100 ml of ethyl acetate. The solution is heated under reflux for 20 minutes and the solvent is then evaporated off. The reaction is followed by TLC; the product is extracted from the reaction medium with a 5% solution of sodium bicarbonate and the product phase is acidified with powdered citric acid and then extracted with ethyl acetate. The organic phase is dried over sodium sulfate and evaporated to give 4.5 g of product.

Yield 88%;
Rf (AcOEt/MeOH/AcOH:95/3/2)=0.38;
$[\alpha]_D$=+101.

NMR SPECTRUM

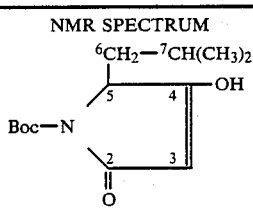

| Delta | Appearance | Integration | Assignment |
|-------|------------|-------------|------------|
| 1.40  | s          | 9 H         | C(CH$_3$)$_3$ |
| 4.85  | s          | 1 H         | 3-CH       |
| 4.33  | q          | 1 H         | 5-CH       |
| 13    | s          | 1 H         | OH         |
| 1.70  | m          | 2 H         | 6-CH$_2$   |
| 1.60  | m          | 1 H         | 7-CH       |
| 0.79  | q          | 6 H         | (CH$_3$)$_2$ |

(4)
(S,S)-1-Tert.-butoxycarbonyl-4-hydroxy-5-isobutyl-2-pyrrolidinone

Compound (V): W'=Boc, $R_1$=CH$_2$CH(CH$_3$)$_2$

The crude product obtained in the previous step is taken up in 100 ml of CH$_2$Cl$_2$ to which 8 ml of acetic acid are added. The solution is stirred in an ice bath, 1.4 g of sodium borohydride are then added in small portions over one hour and the mixture is stirred vigorously for 4 hours. The reaction medium is hydrolyzed with ice and the pH of the aqueous solution is kept between 3 and 4 by adding 0.5 N hydrochloric acid. The organic phase is washed with water, dried over magnesium sulfate and evaporated. The reduced product is purified by chromatography on 300 ml of silica gel, eluting with a mixture of equal volumes of hexane and ethyl acetate, to give 3.6 g of the expected compound.

Yield: 70% relative to the starting hydrated Boc-leucine;
m.p.=90°-91° C.;
Rf (hexane/AcOEt:1/3)=0.58;
$[\alpha]_D$+63.

NMR SPECTRUM

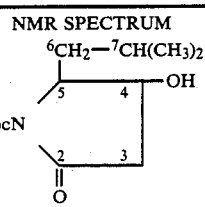

| Delta | Appearance | Integration | Assignment |
|-------|------------|-------------|------------|
| 1.45  | s          | 9 H         | (CH$_3$)$_3$ |
| 2.45  | qd         | 2 H         | 3-CH$_2$   |
| 4.30  | q          | 1 H         | 4-CH       |
| 4.0   | m          | 1 H         | 5-CH       |
| 5.20  | m          | 1 H         | OH         |
| 1.38  | m          | 1 H }       | 6-CH$_2$   |
| 2.75  | m          | 1 H }       |            |
| 2.75  | m          | 1 H         | 7-CH       |
| 0.90  | dd         | 6 H         | (CH$_3$)$_2$ |

(5)
(3S,4S)-4-Tert.-butoxycarbonylamino-3-hydroxy-6-methylheptanoic acid

The product obtained in the previous step is taken up in 15 ml of acetone, and 14 ml of N sodium hydroxide solution are added dropwise. The hydrolysis, which is followed by TLC, is complete after a reaction time of 5 minutes. The pH is brought to 3-4 by adding 1 N hydrochloric acid, after which 200 ml of ethyl acetate and 100 ml of water are added. The organic solution is washed with water, dried over magnesium sulfate and evaporated. The crude reaction product is taken up in 15 ml of acetone and then crystallized by adding 100 ml of hexane to give 3.48 g of a white powder.

Yield: 63% relative to the starting hydrated Boc-leucine;
Rf (CH$_2$Cl$_2$/MeOH/AcOH:93/5/2)=0.43;
$[\alpha]_D$=−41°.

| NMR SPECTRUM |            |             |            |
|-------|------------|-------------|------------|
| Delta | Appearance | Integration | Assignment |
| 1.36  | s          | 9 H         | (CH$_3$)$_3$ |
| 2.22  | q          | 2 H         | CH$_2$     |
| 3.81  | m          | 1 H         | CH-OH      |
| 3.50  | m          | 1 H         | CH-NH      |
| 6.22  | d          | 1 H         | NH         |
| 1.55  | m          | 1 H         | CH         |
| 1.26  | m          | 2 H         | CH$_2$     |
| 0.85  | d          | 6 H         | (CH$_3$)$_2$ |

EXAMPLE 2

Methyl (3S,4S)-4-tert.-butoxycarbonylamino-3-hydroxy-6-methylheptanoate

This compound is obtained from the one prepared in Example 1, step 4: (S,S)-1-tert.-butoxycarbonyl-4-hydroxy-5-isobutyl-2-pyrrolidinone.

257 mg of this product are dissolved in 5 ml of methanol, after which 0.6 ml of a 2 N solution of sodium methanolate is added. After 10 minutes at room temperature, the solution is concentrated, taken up in a 5% aqueous solution of potassium bisulfate and then extracted with ethyl acetate. The organic phase is washed with water, dried over sodium sulfate and evaporated. After passing through a column of silica eluted with ether, the expected product is crystallized from cold hexane to give 260 mg.
Yield: 90%;
Rf (hexane/AcOEt:1/1)=0.77;
[α]$_D$=−40;
m.p.=57°-58° C.

NMR SPECTRUM

BocNH—⁴CH—³CH—²CH₂—COOCH₃
            |        |
       ⁵CH₂—⁶CH(CH₃)₂   OH

| Delta | Appearance | Integration | Assignment |
|---|---|---|---|
| 1.37 | s | 9 H | (CH₃)₃ |
| 6.28 | d | 1 H | NH |
| 3.83 | m | 1 H | CHOH |
| 3.51 | m | 1 H | CHNH |
| 4.78 | d | 1 H | OH |
| 3.57 | s | 3 H | OCH₃ |
| 2.30 | qd | 2 H | 2-CH₂ |
| 1.25 | m | 2 H | 5-CH₂ |
| 1.54 | m | 1 H | 6-CH |
| 0.84 | dd | 6 H | (CH₃)₂ |

EXAMPLE 3

(3S,4S)-4-Tert.-butoxycarbonylamino-3-hydroxy-5-phenylpentanoic acid (1)

(S)-5-(2-Tert.-butoxycarbonylamino-1-hydroxy-3-phenylpropylidene)-2,2-dimethyl-1,3-dioxane-4,6-dione Compound (III): W'=Boc, R₁=CH₂C₆H₅

2.65 g of Boc-Phe-OH, 2.7 g of dimethylaminopyridine and 1.6 g of Meldrum's acid are mixed in 30 ml of methylene chloride. The solution is cooled to −7° C. and 1.3 ml of isopropenyl chloroformate in 20 ml of methylene chloride are added slowly over 1 hour. After 2 hours at −7° C., the mixture is washed with a 5% solution of potassium bisulfate and then with a saturated solution of sodium chloride. Evaporation of the solvent leads to the formation of a white precipitate; the condensation reaction is quantitative. The product obtained is used as such or after purification. The precipitate is taken up in a solution of equal volumes of methanol and ether to give 3 g of the expected product in the form of a white precipitate. Non-purified product remains in the mother liquor.
Yield: 77%.

The expected product can also be prepared in the presence of a coupling agent. 1.33 g of Boc-Phe-OH, 750 mg of Meldrum's acid and 900 mg of 4-dimethylaminopyridine are mixed in 20 ml of methylene chloride at room temperature and 1.2 g of dicyclohexylcarbodiimide are added. The rapid formation of a white precipitate is observed and the reaction medium becomes yellow. After 3 hours at room temperature, the medium is concentrated and taken up in ethyl acetate, the precipitate is filtered off and the solution is washed with a 5% solution of potassium bisulfate and then with a saturated solution of sodium chloride, dried over sodium sulfate and evaporated. The mixture is taken up in a solution of equal volumes of methanol and ether to give 300 mg of the expected product in the form of a white precipitate.
Yield: 15%;
m.p.=120°-121° C.;
[α]$_D$ (DMF, c=1)=+88;
Rf (AcOEt/MeOH/AcOH:95/3/2)=0.71.

NMR SPECTRUM (¹⁴CH₃)₃—¹³C—O—¹²C—NH—⁴CH—³C=² ... ⁵CH₂—C₆H₅(6,7,8,9) ... ¹¹CH₃/¹⁰/¹¹CH₃ ... OH ... O

| Delta | Appearance | Integration | Assignment |
|---|---|---|---|
| 11.66 | s broad | 1 H | OH |
| 5.57 | m | 1 H | 4-H |
| 2.88 | m | 1 H | 5-H |
| 7.36 | d | 2 H | |
| 7.28 | t | 2 H | C₆H₅ |
| 7.20 | t | 1 H | |
| 7.42 | d | 1 H | NH |
| 1.29 | s | 9 H | C(CH₃)₃ |
| 1.66 | s | 6 H | (CH₃)₂ |

Carbon 13 NMR SPECTRUM

| Delta | Appearance | Assignment |
|---|---|---|
| 165 | s broad | C1 |
| 90 | s | C2 |
| 195 | s | C3 |
| 55 | d | C4 |
| 47 | t | C5 |
| 137 | s | C6 |
| 128 | d | C8 |
| 130 | d | C7 |
| 126 | d | C9 |
| 105 | s | C10 |
| 26 | q | C11 |
| 155 | s | C12 |
| 78 | s | C13 |
| 27 | q | C14 |

(2)

(S)-1-Tert.-butoxycarbonyl-4-hydroxy-5-benzyl-1,2-dihydro-2-pyrrolone

Compound (IV-IVa)L: W'=Boc, R₁=CH₂C₆H₅

800 mg of the compound obtained in the previous step are heated under reflux in 20 ml of methanol for 20 minutes. After evaporation of the solvent, the product is dissolved in ether and crystallized by adding hexane to give 570 mg of the expected product.
Yield: 95%, i.e. 88% relative to the starting Boc—Phe—OH;
m.p.=141°-142° C.;
[α]$_D$=+230;
Rf (AcOEt/MeOH/AcOH:95/3/2)=0.48.

NMR SPECTRUM

⁶CH₂C₆H₅
           \
            ⁵—⁴—OH
BocN ¹    /
        \₂—³
          ‖
          O

| Delta | Appearance | Integration | Assignment |
|---|---|---|---|
| 1.5 | s | 9 H | C(CH₃)₂ |
| 4.66 | s | 1 H | 3-CH |
| 4.60 | q | 1 H | 5-CH |

-continued

NMR SPECTRUM

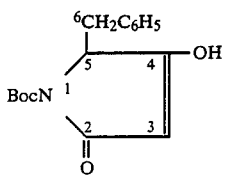

| Delta | Appearance | Integration | Assignment |
|---|---|---|---|
| 3.21 | m | 2 H | 6-CH$_2$ |
| 7.0 | m | 2 H | C$_6$H$_5$ |
| 7.2 | m | 3 H | |

(3)
(S,S)-1-Tert.-butoxycarbonyl-4-hydroxy-5-benzyl-2-pyrrolidinone

Compound (V): W'=Boc, R$_1$=CH$_2$C$_6$H$_5$

The compound is obtained by following the procedure described in Example 1, step 4.
M.p.=120°–122° C.;
[α]$_D$=+43;
Rf (hexane/AcOEt:1/3)=0.58.

NMR SPECTRUM

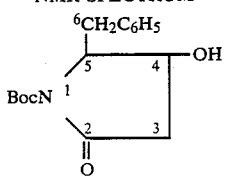

| Delta | Appearance | Integration | Assignment |
|---|---|---|---|
| 1.35 | s | 9 H | (CH$_3$)$_3$ |
| 2.37 | qd | 2 H | 3-CH$_2$ |
| 4.30 | m | 1 H | 4-CH |
| 4.25 | m | 1 H | 5-CH |
| 5.5 | d | 1 H | OH |
| 3.0 | qd | 2 H | 6-CH$_2$ |
| 7.25 | m | 5 H | C$_6$H$_5$ |

(4)
(3S,4S)-4-Tert.-butoxycarbonylamino-3-hydroxy-5-phenylpentanoic acid

Compound (I): W=Boc, R$_1$=CH$_2$C$_6$H$_5$, R$_2$=H

This compound is obtained by following the procedure described in Example 1, step 5.
[α]$_D$=−36;
Rf (CH$_2$Cl$_2$/MeOH/AcOH:95/5/2)=0.44.

| | NMR SPECTRUM | | |
|---|---|---|---|
| Delta | Appearance | Integration | Assignment |
| 1.29 | s | 9 H | C(CH$_3$)$_3$ |
| 2.29 | qd | 2 H | CH$_2$ |
| 3.88 | m | 1 H | CH—OH |
| 3.66 | m | 1 H | CH—NH |
| 6.49 | d | 1 H | NH |
| 2.7 | qd | 2 H | CH$_2$-C$_6$H$_5$ |
| 7.2 | m | 5 H | C$_6$H$_5$ |

EXAMPLE 4

(3R,4R)-4-Tert.-butoxycarbonylamino-3-hydroxy-5-phenylpentanoic acid

This product is prepared by following the procedure described in Example 3, starting from (D)-Boc-Phe-OH. The products obtained in each step differ from those obtained in the corresponding steps of the previous example by having opposite optical rotations.

(1)
(R)-5-(2-Tert.-butoxycarbonylamino-1-hydroxy-3-phenylpropylidene)-2,2-dimethyl-1,3-dioxane-4,6-dione Compound (III): W'=Boc, R$_1$=CH$_2$C$_6$H$_5$
M.p.=118°–120° C.;
[α]$_D$ (DMF, c=1)=−87.5.

(2)
(R)-1-Tert.-butoxycarbonyl-4-hydroxy-5-benzyl-1,2-dihydro-2-pyrrolone

Compound (IV-IVa): W'=Boc, R$_1$=CH$_2$C$_6$H$_5$
Rf (AcOEt/MeOH/AcOH:95/3/2)=0.48;
m.p.=148°–149° C.;
[α]$_D$=−230.

(3)
(R,R)-1-Tert.-butoxycarbonyl-4-hydroxy-5-benzyl-2-pyrrolidinone

Compound (V): W'=Boc, R$_1$=CH$_2$C$_6$H$_5$
Rf (hexane/AcOEt)=0.58;
m.p.=119°–120° C.;
[α]$_D$=−43.5.

(4)
(3R,4R)-4-Tert.-butoxycarbonylamino-3-hydroxy-5-phenylpentanoic acid

Rf (CH$_2$Cl$_2$/MeOH/AcOH:93/5/2)=0.44;
m.p.=146°–148° C.;
[α]$_D$=+35.

EXAMPLE 5

Methyl (3S,4S)-4-benzyloxycarbonylamino-3-hydroxypentanoate (1)
(S)-1-Benzyloxycarbonyl-4-hydroxy-5-methyl-1,2-dihydro-2-pyrrolone Compound (IV-IVa): W'=Z, R$_1$=CH$_3$ This compound is prepared by following the method described in Example 1, step 3.
Yield calculated relative to the starting amino acid (Z—Ala—OH): 89%;
Rf (AcOEt/MeOH/AcOH:95/3/2)=0.33;
[α]$_D$=+60.5.

NMR SPECTRUM

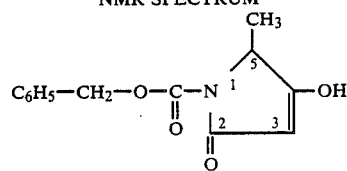

| Delta | Appearance | Integration | Assignment |
|---|---|---|---|
| 7.4 | m | 5 H | C$_6$H$_5$ |
| 5.22 | q | 2 H | CH$_2$ |
| 4.88 | s | 1 H | 3-CH |
| 4.41 | q | 1 H | 5-CH |
| 12.38 | s | 1 H | OH |
| 1.39 | d | 3 H | CH$_3$ |

(2)
(S)-1-Benzyloxycarbonyl-4-hydroxy-5-methyl-2-pyrolidinone

Compound (V): W=Z, R$_1$=CH$_3$

This compound is prepared by following the method described in Example 1, step 4.

Yield calculated relative to the starting amino acid: 58%;

Rf (hexane/AcOEt:1/3)=0.36;

[α]$_D$= +50.

MNR SPECTRUM

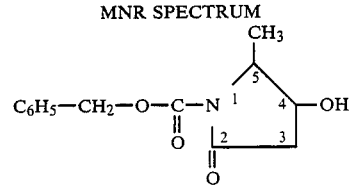

| Delta | Appearance | Integration | Assignment |
|---|---|---|---|
| 7.40 | m | 5 H | C$_6$H$_5$ |
| 5.21 | q | 2 H | CH$_2$ |
| 2.54 | qd | 2 H | 3-CH$_2$ |
| 4.82 | q } J = 6.6 Hz | 1 H | 4-CH |
| 4.15 | m } | 1 H | 5-CH |
| 5.35 | | 1 H | OH |
| 1.2 | d | 3 H | CH$_3$ |

(3) Methyl (3S,4S)-4-benzyloxycarbonylamino-3-hydroxypentanoate

Compound (I): W=Z, R$_1$=CH$_3$, R$_2$=CH$_3$ 500 g of the product obtained in the previous step are taken up in 5 ml of methanol, and 1.5 ml of an approximately 2 N solution of hydrogen chloride in methanol are added. The reaction medium is heated under reflux for 20 minutes, the solvent is then evaporated off, the reaction product is taken up in methanol and the mixture is evaporated to drive off the excess acid. After chromatography on a column of silica gel eluted with ether, the product is crystallized from an ether/hexane mixture, 8/2 by volume, to give 525 mg of the expected compound.

Yield 93%;
Rf (hexane/AcOEt:1/1)=0.44;
m.p.=90°-92° C.;
[α]$_D$=−17.5.

NMR SPECTRUM

| Delta | Appearance | Integration | Assignment |
|---|---|---|---|
| 7.35 | m | 5 H | C$_6$H$_5$ |
| 5.02 | s | 2 H | CH$_2$-C$_6$H$_5$ |
| 6.96 | d | 1 H | NH |
| 3.90 | m | 1 H | CHOH |
| 3.62 | m | 1 H | CHNH |
| 4.81 | broad | 1 H | OH |
| 3.58 | s | 3 H | OCH$_3$ |
| 2.35 | qd | 2 H | CH$_2$-CO$_2$ |
| 1.03 | d | 2 H | CH$_3$ |

EXAMPLE 6

(3S,4S)-4-Benzyloxycarbonylamino-3-hydroxypentanoic acid

This compound is prepared from the product obtained in Example 5, step 2. 1.25 g of this compound are taken up in 20 ml of dioxane, 5 ml of 1 N hydrochloric acid are added and the mixture is then heated under reflux for 2 hours. The solvent is concentrated and the reaction medium is taken up in water and extracted with ethyl acetate; the organic solution is extracted with 50 ml of a 5% solution of sodium bicarbonate. The aqueous phase is neutralized with powdered citric acid and extracted with ethyl acetate. The organic phase is washed with water and then with a saturated solution of sodium chloride, dried and evaporated to give 1.1 g of the expected compound.

Yield 83%;
Rf (CH$_2$Cl$_2$/MeOH/AcOH:93/5/2)=0.27;
[α]$_D$=−15.

NMR SPECTRUM $$C_6H_5-CH_2-O-C-NH-{}^4CH-{}^3CH-{}^2CH_2-COOH$$
with $^5CH_3$ on $^4CH$, =O on C, and OH on $^3CH$

| Delta | Appearance | Integration | Assignment |
|---|---|---|---|
| 7.40 | m | 5 H | C$_6$H$_5$ |
| 5.22 | q | 2 H | CH$_2$ |
| 2.53 | qd | 2 H | 2-CH$_2$ |
| 4.32 | m | 1 H | 3-CH |
| 4.16 | m | 1 H | 4-CH |
| 5.36 | d | 1 H | NH |
| 1.22 | d | 3 H | CH$_3$ |

The compounds (I) according to the invention which are described in Table 1 were prepared using the same methods as in the preceding examples. Having been obtained from natural amino acids in the L configuration, these compounds all have the (3S,4S) configuration. These products were characterized by their optical rotation ([α]$_D$), their Rf, if appropriate their melting point (m.p.) (Table 2) and their NMR spectrum (Table 3 for the compounds in which R$_2$=H and Table 4 for the compounds in which R$_2$=CH$_3$).

TABLE 1

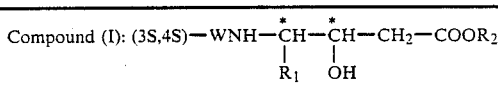

| Example no. | W | R$_1$ | R$_2$ |
|---|---|---|---|
| 7 | Boc | CH(CH$_3$)$_2$ | H |
| 8 | " | " | CH$_3$ |

TABLE 1-continued

Compound (I): (3S,4S)—WNH—*CH—*CH—CH$_2$—COOR$_2$
                              |      |
                              R$_1$   OH

| Example no. | W | R$_1$ | R$_2$ |
|---|---|---|---|
| 9 | " | CH$_2$C$_6$H$_5$ | CH$_3$ |
| 10 | " | CH$_2$OCH$_2$C$_6$H$_5$ | H |
| 11 | " | " | CH$_3$ |
| 12 | " | CH$_2$CH$_2$SCH$_3$ | H |
| 13 | " | " | CH$_3$ |
| 14 | " | 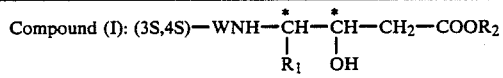 | H |
| 15 | " | " | CH$_3$ |
| 16 | " | (CH$_2$)$_4$NHZ | H |
| 17 | " | " | CH$_3$ |
| 18 | " | CH$_2$C$_6$H$_{11}$ | H |

TABLE 2

Physico-chemical characteristics of the compounds (I)

| Example no. | Rf | M.p. °C. | $[\alpha]_D$ |
|---|---|---|---|
| 7 | (a) 0.45 | | −43 |
| 8 | (b) 0.74 | | (c) −42 |
| 9 | (b) 0.66 | 97–98 | −35 |
| 10 | (a) 0.47 | | −3.5 |
| 11 | (b) 0.69 | | −5 |
| 12 | (a) 0.40 | 107–108 | −30.6 |
| 13 | (b) 0.56 | | −31 |
| 14 | (a) 0.32 | 162–164 | −39 |
| 15 | (b) 0.56 | | −31 |
| 16 | (a) 0.40 | 99–100 | −19.5 |
| 17 | (b) 0.35 | | −19 |
| 18 | (d) 0.17 | 100–101 | −35,20 |

(a) Rf (CH$_2$Cl$_2$/MeOH/AcOH: 93/5/2)
(b) Rf (hexane/AcOEt: 1/1)
(c) (0.5 molar in MeOH)
(d) Rf (AcOEt/MeOH: 9/1)

TABLE 3

NMR spectrum of the compounds (I) in which R$_2$ = H (CH$_3$)$_3$C—OCNH—$^4$CH—$^3$CH—$^2$CH$_2$—$^1$COOH
          ‖           |     |
          O          R$_1$  OH Analysis of the chemical shifts, delta.

| Example no. | (CH$_3$)$_3$ 9H s | H2 2H qd | H3 1H m | H4 1H m | NH 1H d | OH 1H d | R$_1$ | |
|---|---|---|---|---|---|---|---|---|
| 7 | 1.37 | 2.22 | 4.02 | 3.04 | 6.06 | | 1H m | 1.71 |
| | | | | | | | 3H d | 0.89 |
| | | | | | | | 3H d | 0.82 |
| 10 | 1.38 | 2.30 | 4.05 | 3.70 | 6.34 | | 5H m | 7.32 |
| | | | | | | | 2H t | 4.46 |
| | | | | | | | 2H q | 3.44 |
| 12 | 1.37 | 2.24 | 3.86 | 3.51 | 6.39 | | 2H m | 2.43 |
| | | | | | | | 3H s | 2.02 |
| | | | | | | | 2H m | 1.71 |
| | | | | | | | and | 1.56 |
| 14 | 1.37 | 2.31 | 3.97 | 3.75 | 6.44 | | 1H s | 10.75 |
| | | | | | | | 1H d | 7.56 |
| | | | | | | | 1H d | 7.3 |
| | | | | | | | 1H s | 7.10 |
| | | | | | | | 1H t | 7.06 |
| | | | | | | | 1H t | 6.98 |
| | | | | | | | 2H qd | 2.84 |
| 16 | 1.37 | 2.24 | 3.86 | 3.38 | 6.26 | | 5H m | 7.33 |
| | | | | | | | 1H m | 7.2 |
| | | | | | | | 2H s | 5.0 |
| | | | | | | | 2H m | 2.98 |
| | | | | | | | 4H m | 1.44 |
| | | | | | | | 2H m | 1.26 |
| 18 | 1.34 | 2 to 2.48 (a) | | 2.93 to 3.78 (b) | 6.21 | | m | 0.62 to 1.78 |

(a) Complex m with 3-CH
(b) Complex m with CH of the cyclohexyl

TABLE 4

NMR spectra of the compounds (I) in which R$_2$ = CH$_3$ (CH$_3$)$_3$C—OCNH—$^4$CH—$^3$CH—$^2$CH$_2$—$^1$COOCH$_3$
          ‖           |     |
          O          R$_1$  OH Analysis of the chemical shifts, delta

| Example no. | (CH$_3$)$_3$ 9H s | H2 2H q | H3 1H m | H4 1H m | NH 1H d | OH 1H d | OCH$_3$ 3H s | R$_1$ | |
|---|---|---|---|---|---|---|---|---|---|
| 8 | 1.38 | 2.32 | 4.05 | 3.04 | 6.10 | 4.64 | 3.57 | 1Hm | 1.72 |
| | | | | | | | | 3Hd | 0.89 |
| | | | | | | | | 3Hd | 0.82 |
| 11 | 1.38 | 2.37 | 4.06 | 3.69 | 6.38 | 4.88 | 3.58 | 5Hm | 7.32 |
| | | | | | | | | 2Hs | 4.46 |
| | | | | | | | | 2Hq | 3.43 |
| 13 | 1.37 | 2.30 | 3.89 | 3.51 | 6.45 | 4.88 | 3.57 | 2Hm | 2.41 |
| | | | | | | | | 3Hs | 2.01 |
| | | | | | | | | 2Hm | 1.71 |
| | | | | | | | | and | 1.56 |
| 15 | 1.36 | 2.40 | 3.99 | 3.77 | 6.45 | 4.99 | 3.56 | 1Hs | 7.62 |
| | | | | | | | | 1Hd | 7.59 |
| | | | | | | | | 1Hd | 7.34 |
| | | | | | | | | 1Hs | 7.12 |
| | | | | | | | | 1Ht | 7.07 |
| | | | | | | | | 1Ht | 6.98 |
| | | | | | | | | 2Hq | 2.85 |
| 17 | 1.36 | 2.30 | 3.88 | 3.37 | 6.31 | 4.83 | 3.58 | 5Hm | 7.32 |
| | | | | | | | | 1Hm | 7.21 |
| | | | | | | | | 2Hs | 5.0 |
| | | | | | | | | 2Hm | 2.98 |
| | | | | | | | | 4Hm | 1.45 |
| | | | | | | | | 2Hm | 1.25 |

The compounds (I) described in Examples 7 to 17 were obtained via the preparation of the corresponding compounds (IV-IVa) and (V) as intermediates. The results relating to the compounds (IV-IVa) are collated in Table 5, which gives in each case the yield relative to the starting amino acid (II), the optical rotation ($[\alpha]_D$), if appropriate the melting point (m.p.) and the Rf of the compound (IV-IVa) and of the compound (III) obtained in the immediately preceding step.

The NMR spectrum of these compounds is described in Table 6. The results relating to the compounds (V) are collated in Table 7, which gives in each case the yield relative to the starting amino acid (II), the Rf, the optical rotation ($[\alpha]_D$) and if appropriate the melting point (m.p.). The NMR spectrum of these compounds is described in Table 8.

TABLE 5

Physico-chemical characteristics of the compounds (IV-IVa)

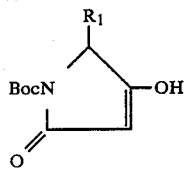

| Ex. no. | $R_1$ | Yield (II) to (IV) | Rf AcOEt/MeOH/AcOH 95/3/2 Compound (III) | Compound (IV-IVa) | $[\alpha]_D$ | M.p. °C. |
|---|---|---|---|---|---|---|
| 7 | $CH(CH_3)_2$ | 91% | 0.52 | 0.42 | +123 | 120-121 |
| 10 (a) | $CH_2OCH_2C_6H_5$ | 80% | 0.68 | 0.46 | +55 | — |
| 12 | $CH_2CH_2SCH_3$ | 85% | 0.61 | 0.44 | | — |
| 14 | 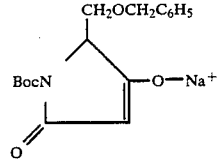 | 86% | 0.62 | 0.42 | +229 | 96-98 |
| 16 | $(CH_2)_4NHZ$ | 82% | 0.61 | 0.28 | +72 | — |

(a) This product is in the form of the sodium salt

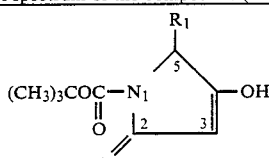

TABLE 6

NMR spectrum of the compounds (IV-IVa)

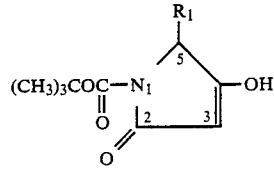

Analysis of the chemical shifts, delta

| Example no. | $(CH_3)_3$ 9H s | H3 1H s | H5 1H m | OH 1H s | $R_1$ | |
|---|---|---|---|---|---|---|
| 7 | 1.42 | 4.85 | 4.25 | 6.19 | 1Hm | 2.33 |
| | | | | | 3Hd | 1.02 |
| | | | | | 3Hd | 0.76 |
| 10 | 1.40 | 4.91 | 4.40 | 12.29 | 2Hm | 3.85 |

TABLE 6-continued

NMR spectrum of the compounds (IV-IVa)

Analysis of the chemical shifts, delta

| Example no. | $(CH_3)_3$ 9H s | H3 1H s | H5 1H m | OH 1H s | $R_1$ | |
|---|---|---|---|---|---|---|
| | | | | | 2Hq | 4.47 |
| | | | | | 5Hm | 7.27 |
| (a) 10 | 1.36 | 3.89 | 3.65 | — | 2Hm | 3.78 |
| | | | | | 2Hq | 4.43 |
| | | | | | 5Hm | 7.27 |
| 12 | 1.45 | 4.88 | 4.46 | 12.38 | 2Hm | 2.0 |
| | | | | | 2Hm | 2.28 |
| | | | | | 3Hs | 1.98 |
| 14 | 1.5 | 4.60 | 4.63 | 12.25 | 2Hm | 3.40 |
| | | | | | 1Hs | 6.89 |
| | | | | | 1Ht | 6.95 |
| | | | | | 1Ht | 7.05 |
| | | | | | 1Hd | 7.32 |
| | | | | | 1Hd | 7.50 |
| | | | | | 1Hs | 10.85 |
| 16 | 1.43 | 4.87 | 4.38 | 12.26 | 2Hm | 1.77 |
| | | | | | 2Hm | 1.37 |
| | | | | | 1Ht | 7.20 |
| | | | | | 2Hm | 2.95 |
| | | | | | 2Hs | 4.98 |
| | | | | | 5Hm | 7.32 |

(a) The spectrum of this compound was also run in a basic medium, the compound then being in the form of the sodium salt

TABLE 7

Physico-chemical characteristics of the compounds (V)

$$\text{BocN} \underset{O}{\overset{R_1}{\diagdown}} \text{—OH}$$

| Example no. | $R_1$ | Yield (II) to (V) | Rf Hexane/AcOEt ⅓ | $[\alpha]_D$ | M.p. °C. |
|---|---|---|---|---|---|
| 7 | $CH(CH_3)_2$ | 57% | 0.55 | +60 | 99-101 |
| 10 | $CH_2OCH_2C_6H_5$ | 78% | 0.52 | +59 | 100-101 |
| 12 | $CH_2CH_2SCH_3$ | 68% | 0.51 | | |
| 14 | $CH_2$–(indole) NH | 70% | 0.38 | +7 | 159-161 |
| 16 | $(CH_2)_4NHZ$ | 60% | | +26 | |
| 18 | $CH_2C_6H_{11}$ | 35.2% | (a) 0.58 | +53.2 | 94 |

(a) Rf (ethyl acetate)

TABLE 8

NMR spectrum of the compounds (V)

$$(CH_3)_3COC\underset{O}{\overset{O}{\|}}-N_1\overset{R_1}{\underset{2}{\diagdown}}\underset{3}{\overset{5}{\diagup}}\overset{4}{-}OH$$

Analysis of the chemical shifts, delta

| Example no. | $(CH_3)_3$ 9H s | H3 2H qd | H4 1H m | H5 1H m | OH 1H d | $R_1$ | |
|---|---|---|---|---|---|---|---|
| 7 | 1.43 | 2.43 | 4.46 | 3.90 | 5.35 | 6Hdd | 0.95 |
| 10 | 1.40 | 2.50 | 4.45 J = 7Hz | 4.10 | 5.45 | 2Hq 2Hq 5Hm | 3.77 4.48 7.30 |
| 12 | 1.44 | 2.48 | 4.33 | 4.04 | 5.38 | 2Hm 2Hm 3Hs | 2.02 to 1.88 2.51 2.05 |
| 14 | 1.35 | 2.40 | 4.30 | 4.30 | 5.49 | 2Hq 1Hd 1Hd 1Ht 1Ht 1Hd 1H | 3.15 7.10 7.6 7.5 6.98 7.92 7.57 |
| 16 | 1.43 | 2.46 | 4.31 | 3.92 | 5.30 | 2Hm 4Hm 2Hq 5Hm 1Ht 2Hs | 1.66 1.33 3.0 7.34 7.2 5.0 |
| 18 | 1.38 | 2.40 | 4.25 | 4.0 | 5.25 | 13Hm | 0.71 to 1.82 |

EXAMPLE 19

Trifluoroacetate of methyl (3S,4S)-4-amino-3-hydroxy-6-methylheptanoate

The compound (I) of Example 8, described in Tables 2 and 4, is prepared from 486 mg of the compound (V) (W'=Boc, $R_1$=$CH(CH_3)_2$) as described in Tables 7 and 8 (Example 7).

The compound (I) in which W=H is then prepared in the following manner: The reaction is carried out by adding 1 ml of a 2 N solution of sodium methanolate in methanol and then, after 10 minutes at room temperature, by adding a solution of hydrogen chloride in methanol; the solvent is evaporated off; the reaction product is taken up in 10 ml of methylene chloride, the solution is then filtered and 2.5 ml of trifluoroacetic acid are added. After 30 minutes at room temperature, the reaction medium is concentrated and the trifluoroacetate salt is precipitated by adding ether. The precipitate is then filtered off, rinsed with ether and dried in a desiccator to give 440 mg of the expected compound.

Yield 80%;
m.p.=140°-142° C.;
$[\alpha]_D = -1$.

NMR SPECTRUM $$\text{H}_2\text{N}-\overset{CH(CH_3)_2}{\underset{}{\text{CH}}}-\overset{}{\underset{\text{OH}}{\text{CH}}}-\text{CH}_2-\text{COOCH}_3 \cdot \text{CF}_3\text{COOH}$$

| Delta | Appearance | Integration | Assignment |
|---|---|---|---|
| 7.72 | s | 2H | $NH_2$ |
| 4.11 | m | 1H | CHOH |
| 2.81 | q | 1H | $CHNH_2$ |
| 5.81 | d | 1H | OH |
| 3.61 | s | 3H | $OCH_3$ |
| 2.61 | q | 2H | $CH_2$ |
| 1.91 | m | 1H | $CH(CH_3)_2$ |
| 0.96 | d | 3H | $CH_3$ |
| 0.92 | d | 3H | $CH_3$ |

What is claimed is:

1. A process for the stereospecific preparation of optically pure (3R,4R)-4-amino-3-hydroxycarboxylic or (3S,4S)-4-amino-3-hydroxycarboxylic acid derivatives of the formula:

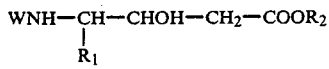 (I)

in which:
W is hydrogen or an N-protecting group;
$R_1$ represents a linear or branched alkyl radical having from 1 to 6 carbon atoms, a methoxy-lower alkyl radical, a benzyloxy-lower alkyl radical, a methylthio-lower alkyl radical, a phenylthio-lower alkyl radical, a benzylthio-lower alkyl radical, an amino-lower alkyl radical which is free or substituted by a protecting group on the amine group, a (lower alkyl)amino-lower alkyl radical, a (lower dialkyl)amino-lower alkyl radical, a hydroxy-lower alkyl radical, a free or esterified carboxy-lower alkyl radical, a free or alkylated carboxamido-lower alkyl radical, a lower alkyl radical substituted at the same time and on the same carbon atom by an amine and a free or esterified carboxyl, a linear or a branched alkenyl radical having from 2 to 6 carbon atoms, a methoxy-lower alkenyl radical such as methoxyvinyl, a phenoxy-lower alkenyl radical, a benzyloxyalkenyl radical, a methylthio-lower alkenyl radical, a phenylthio-lower alkenyl radical, a benzylthio-lower alkenyl radical, an amino-lower alkenyl radical which is free or protected on the amine group, a (lower alkyl)amino-lower alkenyl radical, a (lower dialkyl)amino-lower alkenyl radical, a free or esterified carboxyalkenyl radical, a free or alkylated carboxamido-lower alkenyl radical or a linear or branched alkynyl radical having from 2 to 6 carbon atoms, or alternatively one of the radicals of the formulae:

Cy—A—, Cy—O—A′— or $R_3$S—A′— in which:
Cy represents an aromatic or alicyclic hydrocarbon radical or a heterocyclic radical containing an oxygen or sulfur atom or one or two nitrogen atoms, Cy optionally being mono-, di- or tri-substituted by hydroxyl, lower alkyl, lower alkoxy, trifluoromethyl, nitro or halogeno radicals,
A represents a single bond or a linear or branched alkylene radical having from 1 to 5 carbon atoms or a linear or branched alkenylene radical having from 2 to 5 carbon atoms,
A′ represents a linear or branched alkylene radical having from 1 to 5 carbon atoms, and
$R_3$ represents an S-protecting group; and
$R_2$ represents hydrogen, an alkali metal or alkaline earth metal, a lower alkyl or a benzyl which is unsubstituted or substituted by a lower alkyl group, a halogen or a nitro group,
which comprises
(a) reacting Meldrum's acid with a protected, optically pure amino acid, in the D or L configuration, of the formula:

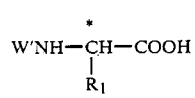 (II)

in which W′ represents an N-protecting group such as Boc or Z, and $R_1$ has the meaning indicated above, in a basic medium, in the presence of an activator for the amino acid (II) or of a coupling agent,
(b) then heating the resulting compound of the formula (III):

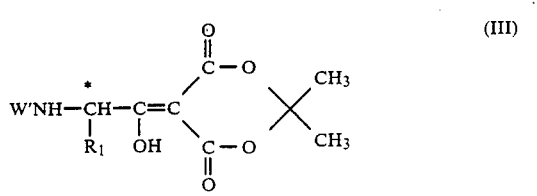 (III)

in which W′ and $R_1$ are as defined above, in a solvent at a temperature of between 30° C. and 100° C.,
(c) then reducing the compound (IV–IVa) thus obtained in 2 tautomeric forms in equilibrium, in which the chirality of the carbon atom carrying the substituent $R_1$ is preserved, the said compound being represented by the following structures:

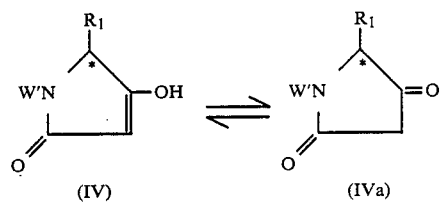

(IV)   (IVa)

in which W′ and $R_1$ are as defined above, with a metal borohydride in an acid medium, or by catalytic reduction under hydrogen pressure when $R_1$ is not sensitive to hydrogenation
(d) opening the ring of the resulting compound V of the formula:

 (V)

in which W′ and $R_1$ are as defined above, either in an acid medium in the case where W′ represents an N-protecting group which is stable in an acid medium, or in a basic medium in the case where W′ represents a sterically hindered N-protecting group which is labile in an acid medium, and, if necessary, finally deprotecting the nitrogen by removing the N-protecting group from the resulting compound of the formula:

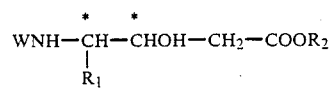

by known methods.
2. The process as claimed in claim 1, wherein:
(1) the amino acid of formula II is Boc-L leucine of formula

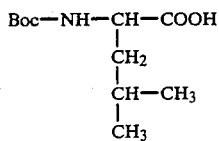

(2) the opening of the ring in step (d) is carried out in a basic medium, and (3) optionally the Boc group is eliminated in order to obtain: the (3S,4S)-4-amino-3-hydroxy-6-methyl-hepanoic acid, i.e. statine.

3. The process of claim 1 wherein (a) the amino acid of formula II is a phenyalanine having the formula:

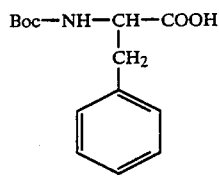

and (b) the opening of the ring in step (d) is carried out in a basic medium.

4. The process of claim 3 further wherein the Boc group is eliminated in order to obtain (3S,4S) 4-tert-butoxy carbonyl amino 3-hydroxy 5-phenylpentanoic acid.

5. The process of claim 1 wherein (a) the amino acid of formula II is a 2-amino 3-cyclohexyl propionic acid having the formula:

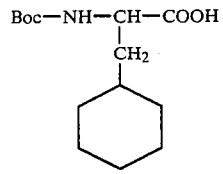

and (b) the opening of the ring in step (6) is carried out in a basic medium.

6. The process of claim 5 further wherein the Boc group is eliminated in order to obtain (3S,4S) 4-tert-butoxy carbonyl amino 3-hydroxy 5-cyclohexylpentanoic acid.

7. The process of claim 1 wherein in step (a) the activator is selected from the group consisting of an acid chloride and an unsaturated chloroformate.

8. The process of claim 1 wherein in step (a) the coupling agent is dicyclohexylcarbodiimide.

9. The process of claim 1 wherein in step (a) the medium is rendered basic by the addition of a base which is selected from the group consisting of pyridine and 4-dimethylaminopyridine and the reaction is carried out at a temperature of between room temperature and $-10°$ C., in an aprotic solvent selected from the group consisting of methylene chloride and ethyl acetate for from 1 to 5 hours.

10. The process of claim 1 wherein in step (c) the metal borohydride is sodium borohydride, the acid medium is an acetic acid medium and step (c) takes place in an aprotic solvent.

11. The process of claim 1 wherein in step (c) the catalytic reduction takes place in the presence of platinum oxide or Raney nickel.

12. The process of claim 1 wherein step (d) takes place in either sodium hydroxide or in an alcoholic solution $R_2OH$, in order to give $COOR_2$ in the final product.

13. The process of claim 1 wherein in step (a) the activator is selected from the group consisting of an acid chloride and an unsaturated chloroformate, or the coupling agent is dicyclohexylcarbodiimide, the medium is rendered basic by the addition of a base which is selected from the group consisting of pyridine and 4-dimethylaminopyridine and the reaction is carried out at a temperature of between room temperature and $-10°$ C. in an aprotic solvent selected from the group consisting of methylene chloride and ethyl acetate for from 1 to 5 hours, further wherein in step (c) the metal borohydride is sodium borohydride, the acid medium is an acetic acid medium and step (c) takes place in an aprotic solvent, or the catalytic reduction takes place in the presence of platinum oxide or Raney nickel and further wherein step (d) takes place in either sodium hydroxide or in an alcoholic solution $R_2OH$ to give $COOR_2$ in the final product.

* * * * *